United States Patent
Ou et al.

(10) Patent No.: US 9,193,645 B2
(45) Date of Patent: Nov. 24, 2015

(54) XYLENE ISOMERIZATION PROCESS AND CATALYST THEREFOR

(71) Applicant: ExxonMobil Chemical Patents Inc., Baytown, TX (US)

(72) Inventors: John Di-Yi Ou, Houston, TX (US); Shifang Luke Luo, Kingwood, TX (US); Surbhi Jain, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 282 days.

(21) Appl. No.: 13/961,530

(22) Filed: Aug. 7, 2013

(65) Prior Publication Data

US 2014/0066675 A1 Mar. 6, 2014

Related U.S. Application Data

(60) Provisional application No. 61/695,493, filed on Aug. 31, 2012.

(51) Int. Cl.
*C07C 5/27* (2006.01)
(52) U.S. Cl.
CPC ........... *C07C 5/2737* (2013.01); *C07C 2529/40* (2013.01)
(58) Field of Classification Search
USPC ........................................................ 585/481
See application file for complete search history.

(56) References Cited

U.S. PATENT DOCUMENTS

| | | |
|---|---|---|
| 5,043,502 A | 8/1991 | Martindale et al. |
| 6,180,550 B1 | 1/2001 | Beck et al. |
| 6,207,871 B1 | 3/2001 | Hellring et al. |
| 6,448,459 B1 | 9/2002 | Magne-Drisch et al. |
| 6,872,866 B1 | 3/2005 | Nemeth et al. |
| 7,244,409 B2 | 7/2007 | Burgfels et al. |
| 7,371,913 B2 | 5/2008 | Bauer |
| 7,439,412 B2 | 10/2008 | Ou et al. |
| 7,495,137 B2 | 2/2009 | Zhou et al. |
| 7,592,499 B2 | 9/2009 | Wolff et al. |
| 7,626,065 B2 | 12/2009 | Ou et al. |
| 7,932,426 B2 | 4/2011 | Bauer |
| 8,273,934 B2 | 9/2012 | Ou et al. |
| 8,344,197 B2 | 1/2013 | Lattner et al. |
| 8,399,727 B2 | 3/2013 | Lattner et al. |
| 2002/0082462 A1 | 6/2002 | Ferraro et al. |
| 2011/0108867 A1 | 5/2011 | Youn |
| 2011/0263918 A1 | 10/2011 | Ou et al. |
| 2012/0108868 A1 | 5/2012 | Pilliod et al. |
| 2012/0316375 A1 | 12/2012 | Zheng et al. |
| 2013/0165724 A1 | 6/2013 | Han et al. |
| 2013/0217940 A1 | 8/2013 | Zheng et al. |

FOREIGN PATENT DOCUMENTS

| | | |
|---|---|---|
| WO | 2010/120616 | 10/2010 |
| WO | 2011/133326 | 10/2011 |

OTHER PUBLICATIONS

U.S. Appl. No. 61/544,491, filed Oct. 7, 2011, Zheng et al.
U.S. Appl. No. 61/625,418, filed Apr. 17, 2012, Porter.

*Primary Examiner* — Thuan D Dang

(57) ABSTRACT

The invention concerns a xylenes isomerization process for the production of equilibrium or near-equilibrium xylenes from a feedstream comprising phenol and/or styrene.

12 Claims, 2 Drawing Sheets

XYLENE ISOMERIZATION PROCESS AND CATALYST THEREFOR

CROSS REFERENCE TO RELATED APPLICATIONS

This application claims priority to and the benefit of Provisional Application No. 61/695,493, filed on Aug. 31, 2012.

FIELD OF THE INVENTION

The invention relates to a xylene isomerization process and catalyst therefor.

BACKGROUND OF THE INVENTION

An equilibrium mixture of xylenes contains about 24 wt % paraxylene (PX), 56 wt % metaxylene (MX), and 20 wt % orthoxylene (OX). PX is relatively high value as compared with MX and OX, since it is a starting material for polyester fibers and resins. Therefore it is advantageous to isomerize OX and/or MX to PX, such as isomer ng a PX-lean stream (i.e., depleted from equilibrium value) to equilibrium for PX recovery. It is an active area, of research.

Typically, xylene streams found in chemical or petrochemical plants also contain ethylbenzene (EB). Conventional isomerization technologies operating at high temperatures (e.g., 400° C.) in vapor phase isomerize the xylenes and dealkylate EB to benzene. Other vapor-phase isomerization technologies convert EB to xylenes in addition to xylenes isomerization. There are also liquid-phase isomerization technologies. Conventional isomerization technologies typically produce significant amounts (>0.5 mol %) of byproducts such as benzene and A9+ (aromatic hydrocarbons having 9 or more carbon atoms), and are also sensitive (e.g., the isomerization catalyst deactivates) to impurities in the feedstream. Most isomerization technologies also require high hydrogen partial pressure to maintain the catalyst activity, which makes the process arrangement complex and expensive.

U.S. Pat. No. 6,180,550 teaches ZSM-5 useful in the liquid phase isomerization of xylene. The zeolite used has a SiO2/Al2O3 ratio of less than 20.

U.S. Pat. No. 6,448,459 teaches isomerization without hydrogen in a liquid phase diluted with toluene used as desorbent in a simulated moving bed adsorptive separation unit. The catalyst used in the liquid phase isomerization is said to be zeolitic, for example ZSM-5, and in the example it is specified that there is no hydrogen.

U.S. Pat. No. 6,872,866 teaches a two stage, liquid or partially liquid phase isomerization process using a zeolitic-based catalyst system preferably based on zeolite beta and on pentasil-type zeolite. This patent also sets forth numerous examples of prior art catalyst systems, including ZSM-5.

U.S. Pat. No. 7,244,409 teaches small crystallite ZSM-5 which may be used for isomerization reactions.

U.S. Pat. No. 7,371,913 teaches a ZSM-5 mole sieve further comprising Ga used as an isomerization catalyst to provide an increased amount of PX in the liquid phase in the substantial absence of $H_2$. The amount of $H_2$ present is stated to be less than 0.05, preferably less than 0.01, mole $H_2$/mole feed.

U.S. Pat. No. 7,495,137 teaches a two-stage isomerization system, the first zone operating in the absence of hydrogen (as in the above patent) using a platinum-free catalyst and the second zone using a catalyst comprising a molecular sieve and a platinum-group to metal component. The catalyst in the first zone is preferably a Ga-MET-type zeolite and it is preferred that the catalyst for the first zone has a Si:Al ratio greater than about 10.

U.S. Pat. No. 7,592,499 teaches a multi-stage process for co-producing PX and styrene from a feed of hydrocarbons comprising xylenes and EB. In the first stage, PX is separated from the feed by means of a simulated moving bed adsorptive separation column to is produce a raffinate comprising EB, OX, and MX. Next, EB in the raffinate is dehydrogenated to styrene. Eventually a stream containing unconverted EB, MX, and OX is obtained and contacted with an isomerization catalyst preferably in the liquid phase. The catalyst is zeolitic, such as ZSM-5.

U.S. Pat. No. 7,932,426 teaches a two-stage isomerization process, the first stage in the liquid phase in the substantial absence of $H_2$ to obtain an intermediate stream. In the second stage, the intermediate stream is mixed with a stream rich in naphthene, and contacted with an isomerization catalyst. By "substantial absence of $H_2$" is meant no free hydrogen is added to a feed mixture and any dissolved hydrogen from prior processing is substantially less than about 0.05 moles/mole of feed. The first isomerization catalyst includes a molecular sieve, typically an aluminosilicate having a $Si:Al_2$ ratio greater than about 10. In the example given, a Ga source is used to make the catalysts for both the first and second isomerization steps.

U.S. Publication No. 2010-0152508 (U.S. application Ser. No. 12/612,007, now allowed) teaches a process for isomerization that is at least partially in the liquid phase and includes a step of removal of C9 aromatic hydrocarbons from a feedstream including C8 and C9 aromatic hydrocarbons.

U.S. Publication No. 2011-0263918 teaches, in embodiments the process takes a PX-lean feedstream to produce a product having equilibrium or near equilibrium xylenes. In embodiments the process produces very low levels of byproducts (such as <0.3 wt. %). Thus, there is no need for additional distillation columns. Furthermore, the technology can operate without the presence of any hydrogen or with only low ppm levels of dissolved hydrogen, making it a simple and cost-effective process.

Other relevant documents include U.S. Pat. Nos. 7,439,412; 7,626,065; U.S. Publication Nos. 2011-0108867; 2012-0108868; and U.S. patent application Ser. No. 13/861,473.

It has recently been discovered that paraxylene-enriched streams from the alkylation of benzene and/or toluene with methanol and/or dimethylether (DME) over acid-active catalysts such as phosphorus-containing ZSM-5 contain oxygenates such as phenol and olefins such as styrene, which are not easily removed from the alkylation reactor feedstreams. The presence of such impurities are believed to be detrimental to numerous downstream processing steps in the conversion of paraxylene to polyester fibers and resins. Methods of treating such phenol and styrene-containing product streams from such sources as the aforementioned alkylation reaction in the presence of acid-active catalyst, reformate streams, imported streams (e.g., contamination by prior cargoes) are known; see U.S. patent application Ser. Nos. 13/618,211; 13/557,605; 13/483,836; 13/487,651; and U.S. Publication Nos. 2011-0092755; 2011-0092756; and references cited therein.

The present inventors have discovered a catalyst system for a liquid isomerization process that survives a low level of styrene and phenols. In embodiments the process takes a PX-lean feedstream comprising at least one of styrene and phenol to produce a product having equilibrium or near equilibrium xylenes. Furthermore, the technology can operate without the presence of any hydrogen or with only low ppm levels of dissolved hydrogen, making it a simple and cost-effective process.

SUMMARY OF THE INVENTION

The invention is directed to a xylenes isomerization process, including a liquid phase isomerization, for the production of equilibrium or near-equilibrium xylenes, comprising passing a paraxylene-depleted aromatic hydrocarbon feedstream containing at least one of phenol and styrene in the amount of about 10 ppm phenol or less and/or 100 ppm styrene or less to a liquid isomerization process in the presence of an appropriate catalyst under suitable process conditions, including a temperature of less than 295° C., preferably less than 260° C. (500° F.) and a pressure sufficient to maintain the xylenes in liquid phase, to produce a product aromatic hydrocarbon process stream having an increased amount of paraxylene relative to said feedstream.

In embodiments the amount of phenol in said feedstream is 5 ppm or less, and in other embodiments the amount of phenol is 2 ppm or less. In embodiments the amount of styrene in said feedstream is 50 ppm or less, and in other embodiments the amount of styrene in said feedstream is 20 ppm or less.

In embodiments there is also at least one step of purification of said feedstream upstream and/or downstream of said liquid isomerization process, wherein said at least one step is selected from removal of at least a portion of styrene in said feedstream and/or removal of at least a portion of phenol in said feedstream.

In embodiments, the liquid phase isomerization process utilizes a catalyst comprising ZSM-5 and/or MCM-49.

In embodiments the catalyst comprises ZSM-5 crystals in the protonated form to (HZSM-5), and further characterized by a crystal size of <0.1 micron and a $SiO_2/Al_2O_3$ molar ratio of about 20-100, preferably 20-50.

In embodiments, the process can be operated in a continuous mode with low ppm levels of $H_2$ in the feed and in other embodiments in a cyclic mode without $H_2$ in feed but with periodic regenerations of the catalyst.

In embodiments, the process is operated in a continuous mode with from 4 to 10 ppm $H_2$ at a temperature of less than 295° C. and total pressure sufficient to maintain the xylenes in the liquid phase.

In embodiments, the process is operated in a cyclic mode without $H_2$ in the feed but with periodic regenerations using greater than 5 ppm $H_2$ in the feed, in embodiments at least 10 ppm $H_2$ in the feed, in other embodiments at least 20 ppm $H_2$ in the feed.

It is an object of the invention to provide a method of processing paraxylene-depleted feedstreams containing at least one of styrene and/or phenol, including a liquid phase isomerization process which, compared to conventional xylenes isomerization processes, provides at least one of the advantages selected from low investment, low operating costs, low byproduct yields, and low xylem loss.

These and other objects, features, and advantages will become apparent as reference is made to the following detailed description, preferred embodiments, examples, and appended claims.

DETAILED DESCRIPTION

Figure 1:
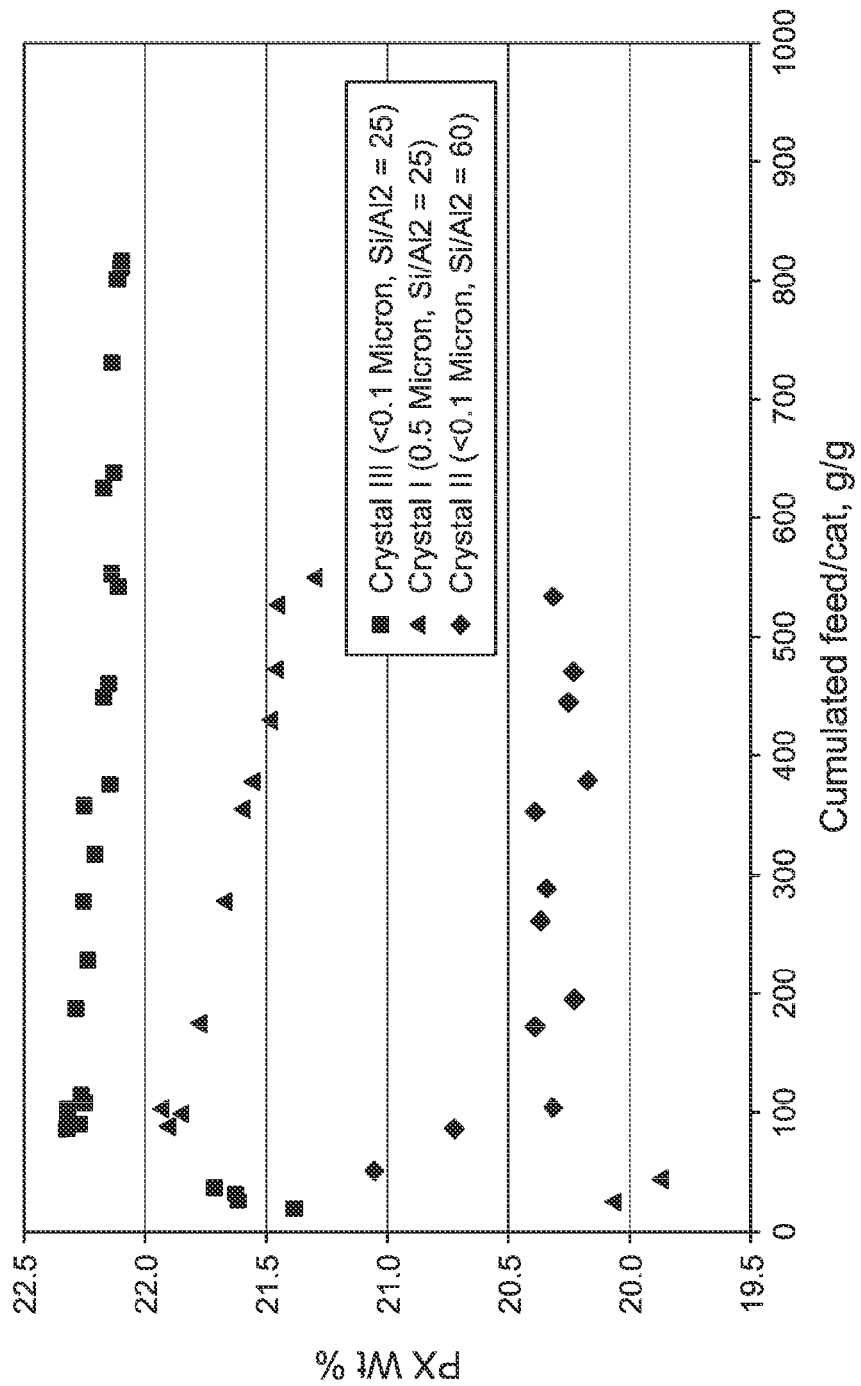
FIG. 1 illustrates paraxylene yields for ZSM-5 crystals of various sizes for embodiments of the liquid phase xylene isomerization process according to the invention.

According to the invention, there is provided a process for the isomerization of a paraxylene-depleted aromatic hydrocarbon feedstream comprising at least one of phenol, styrene, and mixtures thereof, wherein phenol is present in the amount of 10 ppm or less, such as 5 ppm or less, or 2 ppm or less, and/or styrene is present in the amount of 100 ppm or less, such as 50 ppm or less, or 20 ppm or less, wherein said isomerization of a paraxylene-depleted feedstream is in the presence of a catalyst comprising MCM-49 and/or an HZSM-5 catalyst, wherein said HZSM-5 catalyst is characterized in embodiments by a crystal size of <0.1 micron and a $SiO_2/Al_2O_3$ molar ratio of about 20-100, preferably 20-50, in a reactor at a temperature of less than 295° C., preferably 260° C. or less, and a pressure sufficient to maintain the xylenes in liquid phase.

The process may use low ppm levels of $H_2$. Preferably, the $H_2$ concentration in the liquid phase in said reactor is less than 100 ppm (wt % unless otherwise specified). In embodiments, the process is operated in a continuous mode with from 4 to 10 ppm $H_2$. In other embodiments the process is operated in a cyclic mode without $H_2$ in the feed but with periodic regenerations using greater than 5 ppm $H_2$ in the feed, in embodiments at least 10 ppm $H_2$ in the feed, in other embodiments at least 20 ppm $H_2$ in the feed. In still other embodiments, a combination of the aforementioned continuous mode and cyclic modes may be utilized.

in embodiments, the process utilizes a catalyst comprising ZSM-5 crystals along with a binder or the ZSM-5 crystals may be self-bound.

In preferred embodiments the ZSM-5 catalyst, if present, can be characterized in any of the embodiments of the invention by one or more of the following characteristics:
 the ZSM-5 is in the proton form (HZSM-5);
 the ZSM-5 has a crystal size of less than 0.1 microns;
 the ZSM-5 has a mesoporous surface area (MSA) greater than 45 $m^2/g$;
 the ZSM-5 has a zeolite surface area (ZSA) to mesoporous surface area (MSA) ratio of less than 9; and
 a silica to alumina weight ratio in the range of 20 to 50.

As used herein, "crystal size" means average crystal size and is conveniently determined by electron microscopy, as is well-known per se in the art. The surface areas may also be determined by methods well-known in the art.

The ZSM-5 catalyst can be formulated using various techniques such as extrusion, pelletization, oil dropping, spray drying, and the like, techniques which are per se well-known in the art. Optionally, binder materials such as alumina, silica, clay, aluminosilicate, may be used in the formulation. In preferred embodiments, the catalyst is characterized by one or more of the following properties with respect to the binder:
 the zeolite:binder weight ratio is from 1:9 to 9:1;
 the binder preferably comprises silica, alumina, and aluminosilicate; and
 the catalyst is preferably extruded using acetic acid as extrusion aid.

The preferred reactor is fixed bed and the flow may be up or down.

In embodiments, the process can be operated in a continuous mode with low ppm levels of $H_2$ dissolved in the feed and in other embodiments in a cyclic mode without the $H_2$ in feed but with periodic regenerations.

By "low ppm" is meant levels which one of ordinary skill in the art would express as "ppm", generally below 100 ppm. The expression "ppm" is weight ppm (wppm) unless otherwise specified.

In embodiments, very low levels of by products are produced, such as less than 1 wt % or preferably less than 0.5 wt % of by products selected from non-aromatic compounds, benzene and A9+ (aromatic hydrocarbons having 9 or more carbon atoms), and mixtures thereof.

The process comprises contacting a feedstream comprising C8 aromatic hydrocarbons with a catalyst suitable for isomerization, preferably a catalyst comprising MCM-49 and/or ZSM-5, preferably a catalyst comprising ZSM-5 and more preferably having one or more of the aforementioned properties and most preferably all of the aforementioned properties, at a temperature below 295° C., preferably below 280° C., and at a pressure sufficiently to keep the reactant in liquid phase. One of skill in the art in the possession of the present disclosure would be able to determine other operating characteristics, such as a lower temperature, within which the present invention may be practiced. Lower limits may be, for instance, above 180° C. or 190° C. or 200° C., or 210° C., and the like. The flow rate (measured as wt-hourly space velocity, "WHSV") can be selected by one of ordinary skill in the art in possession of the present disclosure, but may advantageously be selected within the range from 1 to 100 $hr^{-1}$ (WHSV), preferably from 1 to 20 $hr^{-1}$ (WHSV), and more preferably from 1 to 10 $hr^{-1}$ (WHSV).

In embodiments, a process for the isomerization of an aromatic hydrocarbon feedstream consisting essentially of a xylenes wherein the concentration of paraxylene is less than about 22 wt % relative to the total C8 aromatic hydrocarbons in said feedstream, and at least one of phenol and styrene, said process comprising:

(a) treating said feedstream to reduce the amount of at least one of phenol and styrene relative to the amount of paraxylene in said aromatic hydrocarbon feedstream, wherein said treating comprises: (i) contact of said feedstream with a material selective for the reduction of phenol relative to styrene and paraxylene; and/or (ii) contact of said feedstream with a material selective for the reduction of styrene relative to phenol and paraxylene, to produce a first product having a reduced concentration of phenol and/or styrene relative to said feedstream in (a), and then (b) isomerizing said first product in the liquid phase in presence of an HZSM-5 catalyst, characterized in embodiments by a crystal size of <0.1 micron and a $SiO_2/Al_2O_3$ molar ratio of about 20-100, in a reactor at a temperature of less than 295° C., preferably 260° C. or less, and a pressure sufficient to maintain the xylenes in liquid phase, to product a second product having an increased amount of paraxylene relative to said feedstream in (a). In preferred embodiments, the feedstream in (a) comprises paraxylene from reformate and/or imported paraxylene. In a more preferred embodiment of the aforementioned embodiment or preferred embodiment, said first product comprises at least one of phenol and styrene, and wherein the amount of phenol is less than 10 ppm, preferably less than 5 ppm, more preferably less than 2 ppm, and the amount of styrene is less than 100 ppm, preferably less than 50 ppm, more preferably less than 20 ppm. The term "selective for reduction of" with respect to phenol and/or styrene means that the specified species is removed or reduce, such as by adsorption, isomerization, and the like, in an amount greater than the removal (again, such as by adsorption, isomerization, and the like) of the other xylenes that the feedstream. As used herein, when the term "consists essentially of" (or similar language) means species which affect the basic and novel features of the invention, styrene, phenol, and the xylene isomers.

Other details of xylenes liquid phase isomerization are available in U.S. Pat. Nos. 7,439,412; 7,626,065; U.S. application Ser. No. 12/612,007, now allowed; and U.S. Publication No. 2011-0263918.

The following experiments are intended to illustrate a process according to present invention and should be taken as representative thereof and not limiting.

EXAMPLE 1

Three ZSM-5 crystals listed below in Table 1 were prepared to investigate the effects of silica/alumina ratio and crystal size in a process according to the present invention.

TABLE 1

| ZSM-5 Crystals | $SiO_2/Al_2O_3$ Ratios | Crystal Sizes, micron |
|---|---|---|
| I | 25 | 0.5 |
| II | 60 | <0.1 |
| III | 25 | <0.1 |

The crystals were ion exchanged to proton form and extruded into 1/20" (about 0.127 cm) extrudates with an alumina binder. The weight ratio of crystal to binder was 4. The extrudates were calcined at 538° C. The extrudates were evaluated using a feed of 13.28 wt % para-xylene, 63.72 wt % meta-xylene, 17.94 wt % ortho-xylene, 1.52 wt % ethylbenzene, 1.28 wt % toluene, and 2.25 wt % non-aromatics, and low levels of benzene and nine-carbon aromatic compounds. The tests were performed in a 1/4" (about 0.635 cm) stainless steel reactor with the feed going up flow through the catalyst bed. Test conditions are listed below to in Table 2.

TABLE 2

| Crystals | Catalyst loading, g | Reactor temp., ° C. | Reactor pressure, psig | Flowrate, Weight Hourly Space Velocity ($hr^{-1}$) |
|---|---|---|---|---|
| I | 0.4550 | 246 | 265 (1928 kPa) | 3.69 |
| II | 0.4545 | 246 | 265 | 3.69 |
| III | 0.4610 | 246 | 265 | 3.74 |

Test results are shown in FIG. 1. It is seen that all three catalysts were able to isomerize meta- and ortho-xylene to para-xylene. However, the paraxylene yield decreased in is the order of III>I>II and that the catalyst with crystal II delivered a near-equilibrium para-xylene yield (97-98% equilibrium). A comparison between Catalysts III and II shows that lowering silica/alumina ratio from 60 to 25 raised para-xylene yield from about 20.2% to about 22.2% and between Catalysts III and I shows that reducing crystal size from 0.5 to <0.1 micron raised para-xylene yield from an average of 21.6% to 22.2%.

EXAMPLE 2

Two parallel runs were conducted to investigate the effect of feed contaminants phenol and styrene on liquid phase isomerization. Catalyst was 1/20" (about 0.127 cm) catalyst extrudates prepared from Catalyst III. Run #1 used Test Feeds and Run #2 used Reference Feeds (free of styrene and phenol). Typical compositions of the two feeds are 3.6-4.7 wt % paraxylene, 57.9-60.4 wt % metaxylene, 24.8-26.0 wt % orthoxylene, 8.7-9.5 wt % ethylbenzene, 0.15-0.19 wt % toluene, 1.2-2.8 wt % non-aromatics, and low levels of benzene and nine-carbon aromatic compounds. Test Feeds contained 20 ppm styrene and 2 ppm phenol.

Performance tests were conducted in a ¼" (0.635 cm) stainless steel reactor with the feed going up flow through a catalyst bed. Test conditions are listed below in Table 3.

TABLE 3

|  | Catalyst loading, g | Reactor temp., ° C. | Reactor pressure, psig | Flowrate, Weight Hourly Space Velocity |
|---|---|---|---|---|
| Run #1 with Test Feed | 0.5056 | 235, 255 | 265 | 1.5-2.6 |
| Run #2 with Reference Feed | 0.5150 | 235, 255 | 265 | 1.8-2.5 |

Figure 2:
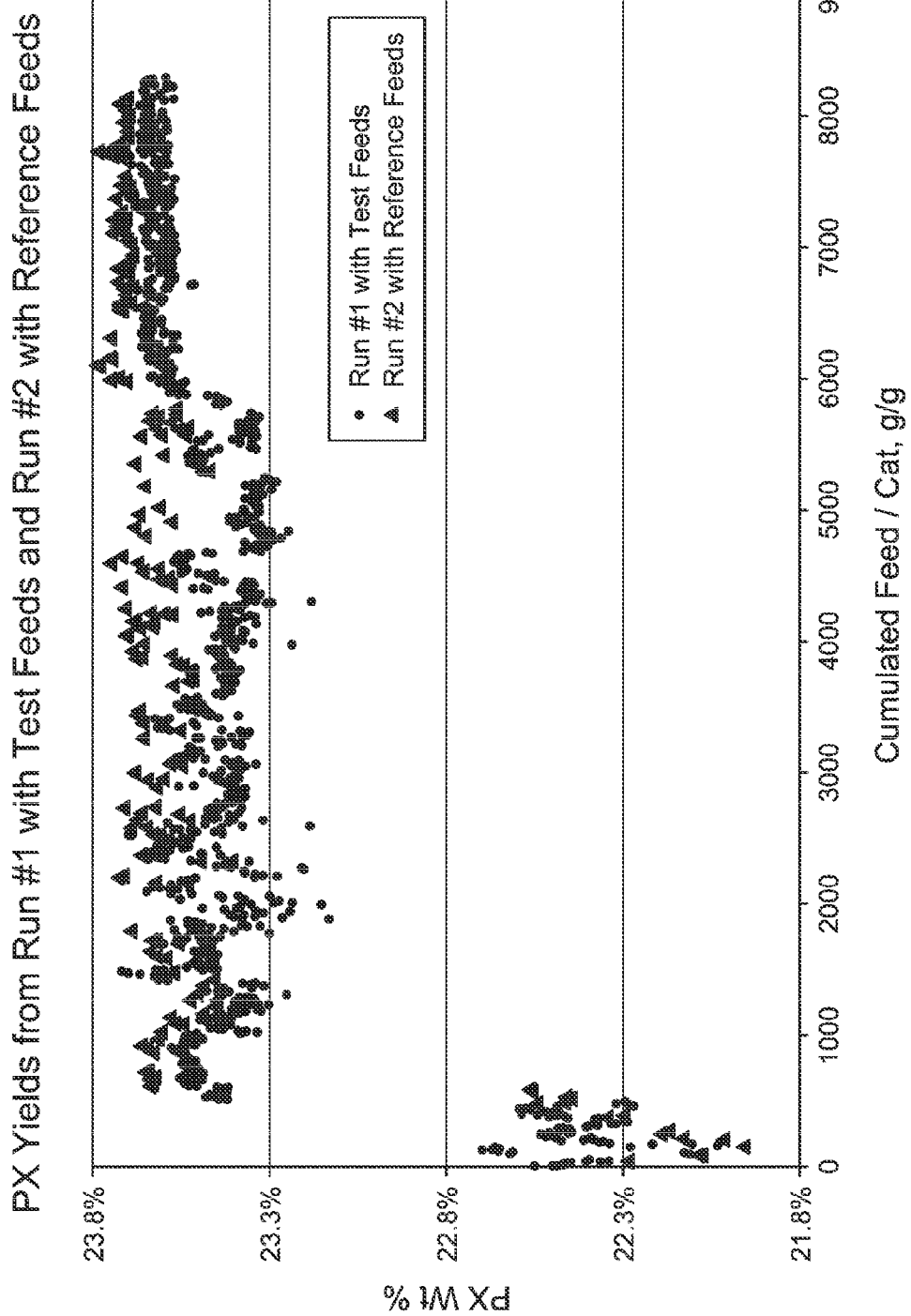
FIG. 2 is a comparison of liquid isomerization of different feeds, illustrating at least one advantage of the present invention.

Test results are shown in FIG. 2. It is seen that both Run #1 with Test Feeds and Run #2 with Reference Feeds achieved near-equilibrium paraxylene yield (97-98% of equilibrium value). Furthermore, a comparison between two runs shows that feed contaminants such as 20 ppm styrene and 2 ppm phenol had no impact on catalyst stability.

EXAMPLE 3

The following experiments were run using the preferred catalyst of the invention on various feedstreams (Table 4) at the same conditions, including a temperature of 255° C. and 2.1 hr$^{-1}$ (WHSV). Experiments were run in a micro-unit; "PX concentration decrease (%)" is paraxylene decrease relative to other C8 aromatic hydrocarbons in the product versus feed, and are extrapolations based on observed trends for six months (run 1 and 2), one week (run 3), and 2 weeks (2 weeks).

TABLE 4

| Run | Phenol, ppm | Styrene, ppm | PX concentration decrease (%) |
|---|---|---|---|
| 1 | 0 | 0 | 0 (i.e. no deactivation) |
| 2 | 2 | 20 | 0 |
| 3 | 2 | 43 | 4.3 |
| 4 | 4 | 20 | 4.7 |

Two styrene concentrations studied were 20 and 43.2 wppm. The temperature of testing was 255° C. for both feeds. Catalyst aging data showed that with 43.2 wpm styrene in the feed, the LPI catalyst deactivated at a rate of 4.3% decrease in PX yield per year (Table 1).

Two phenol concentrations studied were 2 and 4 wppm. Temperatures of testing were 255 and 275° C. for the 2 wppm phenol feed, and 255, 265, and 275° C. for the 4 wppm phenol feed. With 2 wppm phenol in the feed, no catalyst aging was observed at either temperature (Table 1). With the 4 wppm phenol in the feed, however, catalyst aging was observed at 255 and 265° C., but not at 275° C.; the aging rates were 4.66% decrease PX yield per year at 255° C. and 0.88% at 265° C. (Table 3).

TABLE 5

Impact of Styrene and Phenol on LPI Catalyst Aging

| Temp, ° C. | WHSV, h–1 | Phenol, wppm | Styrene, wppm | Catalyst Aging Rate (Drop in absolute PX Yield per year) |
|---|---|---|---|---|
| 255 | 2.1 | 2 | 20 | 0 |
| 255 | 2.1 | 4 | 20 | 4.66% |
| 265 | 2.1 | 4 | 20 | 0.88% |
| 275 | 2.1 | 4 | 20 | 0 |
| 255 | 2.1 | 2 | 43.2 | 4.30% |

In an embodiment, a. PX-lean xylenes feedstream is fed to at least one reactor. "PX-lean", for the purposes of the present invention, means less than equilibrium amount of paraxylene, i.e., less than 24 mol % PX, based on 100 mol % xylene feedstream. In preferred embodiments, the feedstream will comprise from 2 to 18 mol % PX, based on 100 mol % xylene feedstream.

In preferred embodiments, there is no $H_2$ in the xylene feedstream. It is difficult to measure $H_2$ in xylene feedstreams with any accuracy at low ppm levels (which may be attempted by such methods as GC techniques commonly known), and therefore the expression "no $H_2$" as used herein is meant no $H_2$ beyond inevitable impurities, and also that there is no purposeful (intentional) addition of $H_2$ in such feedstreams. The feedstreams may also be purged with an inert gas, such as $N_2$, to reduce even "inevitable impurities" of $H_2$, if so desired. The expression "$H_2$-free", also used herein, is intended to mean the same thing as "no $H_2$". In embodiments, it will be sufficient for the purposes of the present invention that the "$H_2$-free" feedstream contain less than or equal to 4 ppm $H_2$. Low ppm amounts of $H_2$ used in the continuous mode will be, preferably, greater than 4 ppm to about 10 ppm (equivalent to 0.00001 moles of $H_2$ per mole of xylenes). However, the amount of $H_2$ may be higher, such as 50 or 100 ppm.

In practice, one way of accomplishing low ppm levels of $H_2$ is by controlling the quantity of $H_2$ added to the "$H_2$-free stream". For instance, we may know that a stream is $H_2$ free because we know what upstream processing it has gone through, such as distillation which would rid a stream of H2 easily. Then by carefully controlling how much $H_2$ is added, we would know the final $H_2$ quantity.

The reactor may be of any type, such as a fixed bed reactor, fluid bed reactor, dense bed reactor, and the like. For example, the reactor could be a tubular fixed bed reactor packed with a catalyst suitable for isomerization of C8 aromatic hydrocarbons, more preferably a catalyst comprising HZSM-5 and/or MCM-49. The feedstream can flow through the reactor in either up-flow or down-flow mode. Such a reactor can be operated at a temperature below 295° C., a flow rate within the range of 0.1 to 100 hr$^{-1}$ (WHSV), and a pressure sufficiently high to keep the feedstream at liquid phase inside the reactor and advantageously maintained so as to achieve the low byproducts yields. The person of ordinary skill in the art, in possession of the present disclosure, can achieve such conditions without more than routine experimentation. Once temperature is set, those skilled in the an can determine what pressure to use to keep it in liquid phase based on xylenes VLE (vapor-liquid-equilibrium) data. By way of example, without intending to be limiting, in embodiments the pressure may be above 100 psia, or preferably above 150 psia.

Depending on the operating conditions, the catalyst may exhibit a slow deactivation. Low ppm levels of dissolved hydrogen in the xylenes feed can completely mitigate such deactivation. Thus, one can run the reactor with a $H_2$-free xylene feed for a period of time, the length of which depends on the selection of operating parameters of the operator, and at the end of the operation, replace the $H_2$-free xylene feed with a $H_2$-containing xylene feed at the same operating conditions. Thus, in this embodiment, $H_2$ is now purposefully added to the feed. Only low ppm levels are necessary. Although, as mentioned above, GC techniques are not particularly good at measuring $H_2$ levels accurately at low ppm levels in a C8 aromatic hydrocarbon feedstream, the presence of $H_2$ at such levels can be estimated based on $H_2$-xylenes VLE. For the purposes of the present invention, when the "$H_2$-free" feedstream is defined as containing 0.00005 moles $H_2$/mole xylenes or less, or 0.00001 moles $H_2$/mole xylenes or less, the $H_2$-containing xylene feed should have greater than 0.00005 moles $H_2$/mole xylenes, or greater than 0.00001 moles $H_2$/mole xylenes, respectively.

It has been surprisingly found that the $H_2$-containing xylene feed will regenerate the catalyst to recover the lost activity. The regeneration period can vary, such as from 1 day to a few weeks. At the end of the regeneration, an operator can replace the $H_2$-containing feed with the $H_2$-free feed and resume the normal operation.

This regeneration technique has at least several advantages. It is easy to implement and cost effective. Hydrogen can readily dissolve in xylenes at the required level. By way of example, at 160 psia, 71 ppm $H_2$ will be dissolved in xylenes at room temperature. It does not require such expensive and complex process equipment as separator and recompressor that is required for the high $H_2$ partial pressure in conventional vapor-phase isomerization technologies. The regeneration is done with a $H_2$-containing xylene feed at the same conditions as that for the normal operation, which means that even during regeneration, the reactor is still producing equilibrium or near equilibrium xylenes; thus would be no productivity loss. In embodiments the operator can increase the $H_2$ concentration during the regeneration to as high as 100% $H_2$ and 0% xylenes and still accomplish the objective.

In another embodiment, low ppm levels of $H_2$ such as 4 to 100 ppm, preferably 4 to 10 ppm (within the standard sampling error possible by current measurement techniques) are dissolved in the xylene feed and fed to the reactor continuously throughout the operation. The $H_2$ at such levels will completely prevent the catalyst deactivation. As a result, in this embodiment, there is provided a process allowing for long, continuous operation without any need to stop for regeneration. In addition to the advantages listed above, in this embodiment a consistently high PX yield is possible at all times.

Purification of the feedstream by removal of phenol and/or styrene may be done by any method known in the art. Methods of removal of phenol and/or styrene or other olefins have been disclosed in U.S. Publication Nos. 2012-0048780; 2012-0316375; U.S. patent application Ser. Nos. 13/618,211; 13/875,373; 13/875,402; and references discussed therein. These processes are particularly advantageously used when the source of phenols and/or styrene are from an alkylation reactor process comprising the contact of methanol and/or dimethylether with benzene and/or toluene in the presence of an acid-active catalyst, particularly a phosphorus-containing ZSM-5 catalyst that has been steamed at a temperature on the order of 1000° F. (538° C.), such as from about 500 to about 650° C. Preferred materials to remove at least a portion of phenol from the feedstream to the isomerization process of the present invention include alumina, silica, molecular sieves, zeolites, basic organic resins, and mixtures thereof; preferred material to remove at least a portion of styrene from the feedstream to the isomerization process of the present invention include MWW molecular sieves, clay, and mixtures thereof, such as at least one of MCM-22, MCM-36, MCM-49, MCM-56, EMM-10 molecular sieves, and Engelhard F-24, Filtrol 24, Filing 25, and Filtrol 62 clays, Attapulgus clay and Tonsil clay.

One of skill in the art in possession of the present disclosure can readily ascertain that phenol and/or styrene can be present in numerous sources of paraxylene. By way of example, such impurities may come from prior cargoes and may be present in imported paraxylene, or it may come from other processes (other than alkylation in the presence of an acid active catalyst) such as reformate. Reformate may have, by way of example, on the order of 200-300 ppm styrene and on the order of 600-800 ppm styrenic species (including dimethyl styrene). These are merely a few of the many sources of paraxylene that need to be purified of phenol and/or styrene in order to become suitable feedstreams for the present process comprising liquid isomerization.

While the illustrative embodiments of the invention have been described with particularity, it will be understood that various other modifications will be apparent to and can be readily made by those skilled in the art without departing from the spirit and scope of the invention.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A process for the isomerization of a paraxylene-depleted aromatic hydrocarbon feedstream comprising phenol, wherein said isomerization of a paraxylene-depleted feedstream is conducted in the presence of a catalyst comprising HZSM-5, wherein said HZSM-5 is characterized by an average crystal size of <0.1 micron and a $SiO_2/Al_2O_3$ molar ratio in the range of about 20-100, in a reactor at a temperature of less than 295° C., and a pressure sufficient to maintain the xylenes in liquid phase to produce an isomerization product.

2. The process of claim 1, wherein said feedstream is characterized as containing phenol in the amount of 10 ppm or less.

3. The process of claim 1, wherein said feedstream is characterized as containing phenol in the amount of 5 ppm or less.

4. The process of claim 1, wherein said feedstream is characterized as containing phenol in the amount of 2 ppm or less.

5. The process of claim 1, further characterized in that said process is operated in a continuous mode with a feedstream containing low ppm levels of dissolved $H_2$ in the range of about 4 to 100 ppm.

6. The process of claim 1, further characterized in that said process is operated in a continuous mode with a feedstream containing low ppm levels of dissolved $H_2$ in the range of about 4 to 20 ppm.

7. The process of claim 1, further characterized in that said process is operated in a cyclic mode with an $H_2$-free feedstream, and further wherein said catalyst is periodically regenerated by a step including contacting said catalyst with an $H_2$-containing feedstream, wherein said $H_2$-free feedstream is characterized as containing less than 4 ppm dissolved $H_2$ and said $H_2$-containing feedstream is characterized as containing about 4 or more ppm dissolved $H_2$.

8. The process of claim 1, wherein said reactor is at a temperature of 260° C. or less.

9. The process of claim 1, including a step of decreasing the amount of phenol upstream of said isomerization.

10. The process of claim 1, wherein said paraxylene-depleted feedstream is characterized as an aromatic hydrocarbon feedstream consisting essentially of a xylenes wherein the concentration of paraxylene is less than about 22 wt % relative to the total C8 aromatic hydrocarbons in said feedstream.

11. The process of claim 9, wherein said decreasing comprises:
   treating a paraxylene-containing feedstream comprising phenol to reduce the amount of at least one of said phenol, wherein said treating comprises:
   (i) contact of said paraxylene-containing feedstream with a material selective for the reduction of phenol relative to paraxylene to produce a first product having a reduced concentration of phenol.

12. The process of claim 11, wherein said paraxylene-containing feedstream comprises paraxylene obtained from reformate, an alkylation reaction, imported paraxylene, and mixtures thereof.

* * * * *